(12) United States Patent
Townsend et al.

(10) Patent No.: US 6,589,241 B1
(45) Date of Patent: Jul. 8, 2003

(54) BONE CLAMP

(75) Inventors: Frank Townsend, Renfrew (CA); Patrick Rousseau, Hardwick, NJ (US); Mark A. Bryant, Auburn, IN (US)

(73) Assignee: Zimmer, Inc., Warsaw, IN (US)

( * ) Notice: Subject to any disclaimer, the term of this patent is extended or adjusted under 35 U.S.C. 154(b) by 178 days.

(21) Appl. No.: 09/689,341

(22) Filed: Oct. 12, 2000

(51) Int. Cl.[7] ................................................. A61F 5/04
(52) U.S. Cl. ........................... 606/54; 606/72; 606/205; 606/207
(58) Field of Search ............................. 506/54, 53, 57, 506/58, 72, 86, 90, 105, 205, 207, 208

(56) References Cited

U.S. PATENT DOCUMENTS

| | | | |
|---|---|---|---|
| 2,631,585 A | * | 3/1953 | Siebrandt ..................... 606/54 |
| 4,475,544 A | | 10/1984 | Reis |
| 4,896,661 A | * | 1/1990 | Bogert et al. ................ 600/219 |
| 5,318,589 A | * | 6/1994 | Lichtman ..................... 600/564 |
| 5,476,479 A | * | 12/1995 | Green et al. ................. 606/205 |
| 5,484,095 A | * | 1/1996 | Green et al. ............. 227/175.1 |
| 5,578,032 A | * | 11/1996 | Lalonde ...................... 606/205 |
| 5,797,919 A | | 8/1998 | Brinson |
| 6,117,158 A | * | 9/2000 | Measamer et al. .......... 606/208 |

* cited by examiner

*Primary Examiner*—Pedro Philogene
(74) *Attorney, Agent, or Firm*—Jacque R. Wilson, Esq.

(57) ABSTRACT

A bone clamp having a ratchet mechanism including ratchet teeth having rounded peaks with curved valleys therebetween and a curved pawl having a curvature similar to the valleys spanning the peaks of the ratchet teeth. The ratchet mechanism of the current invention distributes the interaction forces between the ratchet teeth and the pawl and therefore is resistive to shear stresses which could otherwise compromise the structural integrity of the ratchet mechanism.

1 Claim, 3 Drawing Sheets

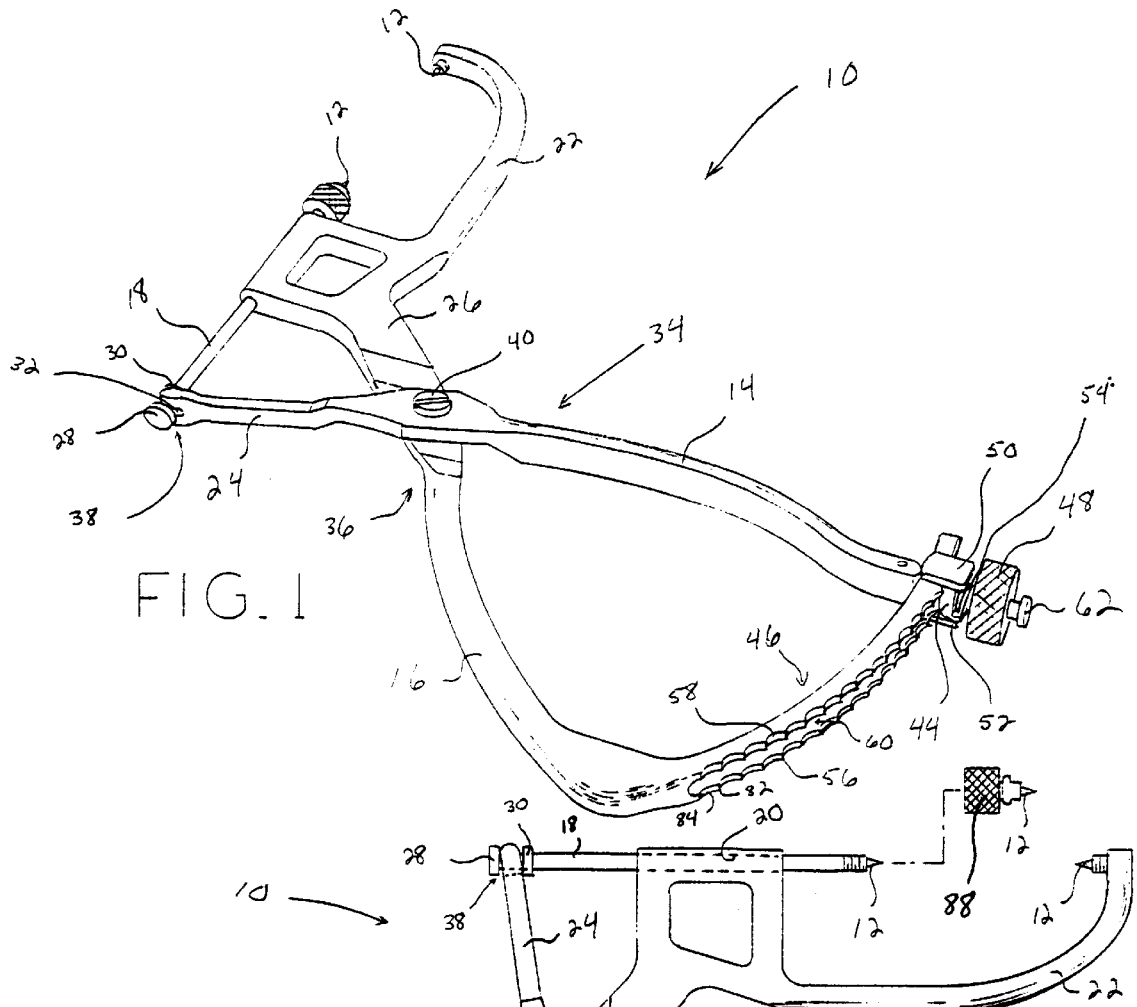

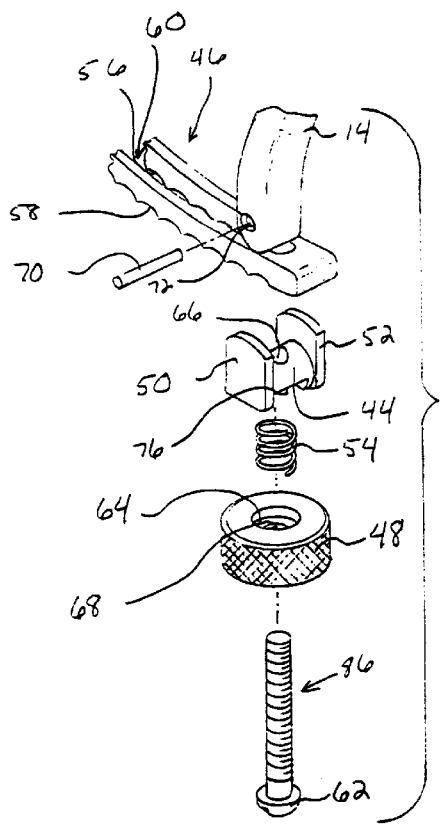
FIG. 3
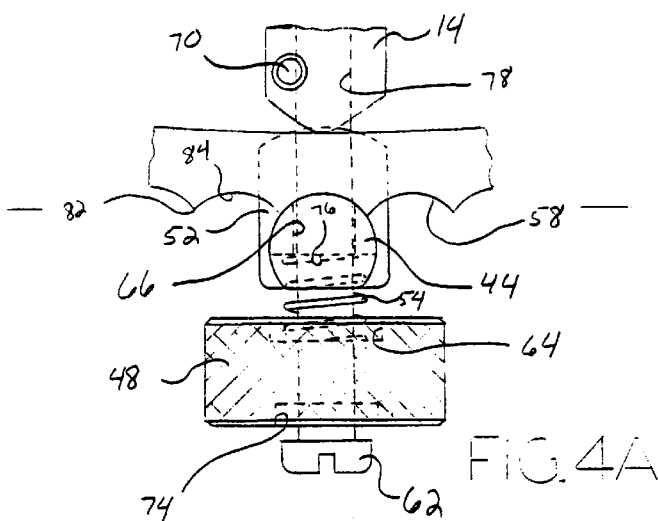
FIG. 4A
FIG. 4B
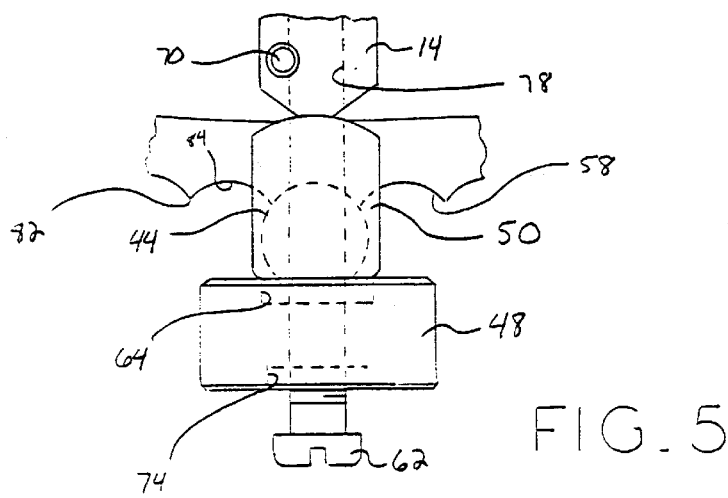
FIG. 5

BONE CLAMP

BACKGROUND OF THE INVENTION

1. Field of the Invention

The present invention relates to bone clamps, and, more particularly, to a bone clamp having an improved rachet mechanism.

2. Description of the Related Art

Bone clamps are well known in the medical profession and can be used, e.g., to engage broken bones for movement thereof. Bone clamps are reusable devices and therefore longevity is a desirable characteristic. Generally, bone clamps are utilized to move broken bones into aligned position or hold bone fragments together while surgical procedures (e.g., installation of a screw, plate, pin, or wire) are performed. When performing surgery to repair a broken bone, it is important to clamp the bone fragments together while a mending device (e.g., a screw, plate, pin, or wire) is being installed so that the bone fragments can be maintained in alignment with substantially no gaps therebetween. For example, bone clamps may be utilized to hold bone plates in position across a bone fracture and/or to align the fractured bones while the bone plate(s) are affixed thereto.

Typically, bone clamps utilize a rachet mechanism to control movement of the bone clamp and to maintain the bone clamp in locked position once it is operatively positioned. Ratchets utilized with prior art bone clamps are generally of two types: (1) a unidirectional rachet, e.g., of the type utilized with standard forceps, and (2) a bidirectional rachet having a selectively actuatable lock mechanism to retain the pawl in locked position between two consecutive rachet teeth.

Ratchets of the second type (i.e., bidirectional ratchets) utilize rachet teeth formed by opposing ramp surfaces 90, 92 as illustrated in FIG. 10. Similarly, pawl 94 is formed by opposing ramp surfaces 96, 98. Opposing ramp surfaces 90, 92 and 96, 98 are substantially linear and culminate in a point. As pawl 94 is moved relative to the ratchet teeth, the peak of the pawl contacts the peaks of successive rachet teeth and the interaction forces between the ratchet and the pawl will be concentrated at the peak of the pawl and the peaks of the ratchet teeth. The concentration of force causes a substantial shear stress at the peaks which will lead to fractures and rounding of the peaks (both of the pawl and of the ratchet teeth) as the bone clamp is repeatedly used. Such rounding of the peaks impairs the utility of the rachet since the pawl will be easily moveable relative to the rachet teeth and there will exist less contact surface area between the pawl and subsequent rachet teeth when the pawl is locked in position therebetween.

Ratchets of the first type (i.e., unidirectional ratchets) are less desirable than bidirectional ratchets since they assist in controlling movement of the clamp actuating members in one direction only. Furthermore, unidirectional ratchets utilize pawls and ratchet teeth having substantially linear ramp surfaces culminating in a point and therefore suffer from the same drawbacks as described above with respect to bidirectional ratchets.

What is needed in the art is a bone clamp having a bidirectional rachet for controlling the movement of the clamp actuating members which does not suffer from the disadvantages described above.

SUMMARY OF THE INVENTION

The present invention comprises a bone clamp having a bidirectional rachet mechanism which does not utilize substantially linear opposing ramp surfaces culminating in a point to form the pawl and the ratchet teeth. The rachet mechanism of the current invention comprises a plurality of rachet teeth formed from a plurality of rounded peaks having a plurality of curved valleys therebetween, and a curved pawl having substantially the same curvature as the valleys of the rachet teeth. The rounded structure of the rachet and pawl of the present invention eliminates the interaction of a pair of sharp peaks as in the prior art. The interaction forces between the rachet and the pawl of the current invention are more evenly distributed than in the ratchet mechanisms of the prior art due to the rounded surfaces of the ratchet teeth and the pawl of the present invention. Therefore, the present invention lessens the detrimental effect of the interaction forces between the ratchet and the pawl.

The invention, in one form thereof, comprises a bone clamp including a first clamp member and a second clamp member as well as a ratchet mechanism, which is resistive to shear stress, for controlling actuation of the first clamp member. Actuation of first clamp member relative to the second clamp member places the bone clamp in either a clamped or an unclamped position.

The invention, in another form thereof, comprises a bone clamp including a first clamp member and a second clamp member as well as a ratchet mechanism for controlling actuation of the first clamp member relative to the second clamp member. The ratchet mechanism of this form of the current invention includes a plurality of ratchet teeth comprising a plurality of curved peaks with a plurality of valleys therebetween, and a pawl which selectively contacts each of the plurality of ratchet teeth.

The invention, in yet another form thereof, comprises a bone clamp including a first clamp member and a second clamp member as well as a ratchet mechanism for controlling actuation of the first clamp member relative to the second clamp member. The ratchet mechanism of this form of the current invention includes a plurality of ratchet teeth comprising a plurality of peaks with a plurality of valleys therebetween and a curved pawl selectively contacting each of the plurality of ratchet teeth.

The invention, in another form thereof, comprises a bone clamp including a first clamp member and a second clamp member as well as a rachet mechanism for controlling actuation of the first clamp member relative to the second clamp member. Actuation of the first clamp member relative to the second clamp member places the bone clamp in either a clamped or an unclamped position. The rachet mechanism of this form of the current invention includes a plurality of rachet teeth comprising a plurality of peaks with a plurality of curved valleys therebetween, and a pawl which selectively contacts each of the plurality of rachet teeth.

An advantage of the present invention is the ability to provide a bidirectional rachet in which interaction forces between the pawl and rachet teeth are more evenly distributed than in the bidirectional ratchets of the prior art.

BRIEF DESCRIPTION OF THE DRAWINGS

The above-mentioned and other features and advantages of this invention, and the manner of obtaining them, will become more apparent and the invention itself will be better understood by reference to the following description of embodiments of the invention taken in conjunction with the accompanying drawings, wherein:

FIG. 1 is a perspective view of a bone clamp in accordance with the present invention;

FIG. 2 is a side elevational view thereof;

FIG. 3 is a fragmentary, exploded, perspective view of a rachet in accordance with the present invention;

FIGS. 4A and 4B are fragmentary side elevational views illustrating the operation of a rachet in accordance with the present invention;

FIG. 5 is a fragmentary side elevational view illustrating the rachet of the present invention in locked position;

Corresponding reference characters indicate corresponding parts throughout the several views. The exemplification set out herein illustrates a preferred embodiment of the invention and such exemplification is not to be construed as limiting the scope of the invention in any manner.

DETAILED DESCRIPTION OF THE INVENTION

Figure 6:
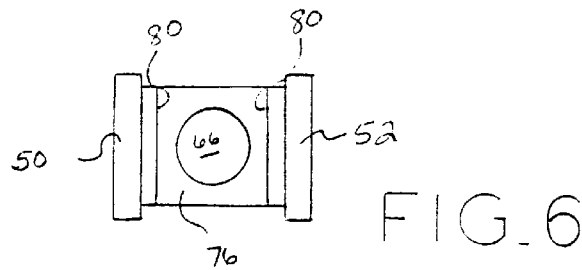
FIG. 6 is a bottom elevational view of a pawl in accordance with the present invention.

Referring now to the drawings, and particularly to FIG. 1, one exemplary embodiment of bone clamp 10 in accordance with the present invention is illustrated. Generally, bone clamp 10 is formed from first clamp member 34, second clamp member 36, ratchet member 46, and clamp plunger 18.

First clamp member 34 is pivotally connected to second clamp member 36 via pivot screw 40. Second clamp member 36 comprises stationary handle 16 and guide member 26. Clamp plunger 18 is operably positioned through guide channel 20 in guide member 26 for axial displacement relative thereto. Guide member 26 further includes support arm 22 holding gripping point 12. Clamp plunger 18 includes gripping point 12 on the distal end thereof. As illustrated in FIG. 2, supplemental grip end 88 can be affixed to clamp plunger 18 to extend the axial length thereof.

First clamp member 34 is formed from moveable handle 14 and actuation member 24 separated by pivot point 42. Actuation member 24 includes Y-shaped end 38 having a slot 32 sized to accommodate clamp plunger 18. Clamp plunger 18 includes first and second flanges 28, 30 (FIG. 2) which are positioned on either side of Y-shaped end 38. Actuation of actuation member 24 causes Y-shaped end 38 to contact either first flange 28, or second flange 30 and thereby actuate clamp plunger 18.

Movement of moveable handle 14 causes actuation of actuation member 24 and consequently clamp plunger 18, thus moving the clamp into operable clamped position. Movement of moveable handle 14 is controlled via rachet member 46. Rachet member 46 comprises two rows of rachet teeth 56, 58 and pawl 44. Rows of rachet teeth 56, 58 are separated by gap 60 and are affixed to, or are integral with stationary handle 16. Pawl 44 is operably connected to moveable handle 14 via pawl connecting screw 62.

As illustrated in FIG. 3, moveable handle 14 is positioned above rows of rachet teeth 56, 58 (moveable handle 14 may or may not contact the portion of ratchet member 46 opposite to rows of rachet teeth 56, 58). Moveable handle 14 includes elongate aperture 78 (FIG. 4A) through which pawl connecting screw 62 may pass. As illustrated in FIG. 3, pawl connected screw 62 traverses threaded lock nut aperture 68 in lock nut 48, spring 54, pawl aperture 66 in pawl 44, and finally elongate aperture 78 in movable handle 14. Retaining pin 70 is positioned through retaining pin aperture 72 and creates an interference fit with pawl connecting screw 62 to resist axial displacement thereof.

FIGS. 4A and 4B illustrate the ratchet of the current invention in assembled form. Lock nut 48 is positioned as illustrated in FIGS. 4A and 4B to allow movement of pawl 44 relative to pawl connecting screw 62 and ratchet teeth 58. Ratchet teeth 58 include peaks 82 with curved valleys 84 therebetween. The curvature of pawl 44 matches the curvatures of valleys 84 as illustrated in FIG. 4A. FIG. 4B illustrates movement of pawl 44 along ratchet teeth 58. As illustrated, pawl 44 moves longitudinally along pawl connecting screw 62 as pawl 44 moves between successive ratchet teeth.

Figure 7:
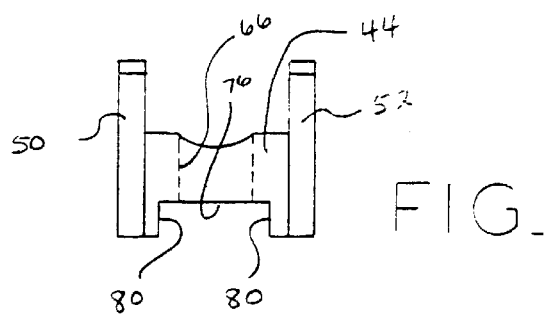
FIG. 7 is a front elevational view thereof.
Figure 8:
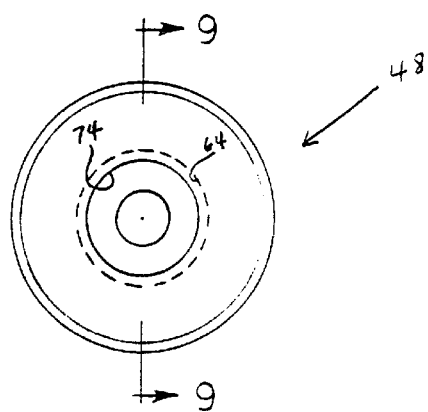
FIG. 8 is an axial elevational view of a lock nut in accordance with the present invention.
Figure 9:
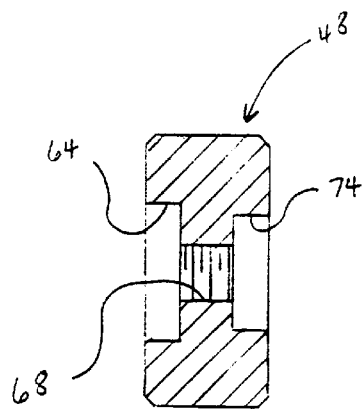
FIG. 9 is a sectional view thereof.
Figure 10:
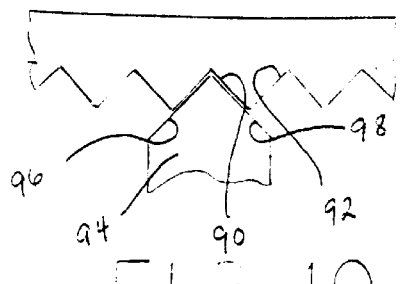
FIG. 10 is a fragmentary side elevational view of a rachet and pawl of the prior art.

Spring 54 biases pawl 44 toward rows of ratchet teeth 56, 58 and encourages contact of pawl 44 with valleys 84. Pawl 44 includes spring contact surface 76 against which an end of spring 54 rests. As illustrated in FIGS. 6 and 7, pawl 44 includes spring retaining surfaces 80 to assist in positioning spring 54 (FIG. 4A) against spring contact surface 76. The opposing end of spring 54 rests against spring recess 64 of lock nut 48. Lock nut 48 further includes screw head recess 74 (FIGS. 8 and 9) which, in one embodiment, will receive the head of pawl connecting screw 62 when lock nut 48 is in unlocked position. As illustrated in FIG. 3, pawl 44 includes first and second pawl guides 50, 52 which, as illustrated in FIG. 1, are positioned on opposing sides of rows of ratchet teeth 56, 58 respectively. First and second pawl guides 50, 52 function to guide pawl 44 as it travels along rows of ratchet teeth 56, 58.

Once the bone clamp is operatively positioned and placed in clamped position, lock nut 48 may be rotated so that threaded lock nut aperture 68 (FIG. 3) interacts with threads 86 of pawl connecting screw 62 to axially displace lock nut 48 and lock pawl 44 in position as illustrated in FIG. 5.

While this invention has been described as having an exemplary design, the present invention can be further modified within the spirit and scope of this disclosure. This application is therefore intended to cover any variations, uses, or adaptations of the invention using its general principals. Further, this application is intended to cover such departures from the present disclosure as come within known or customary practice in the art to which this invention pertains and which fall within the limits of the appended claims.

What is claimed is:

1. A bone clamp, comprising:

a first clamp member, wherein said first clamp member comprises a moveable handle and an actuation member having a Y-shaped end and a slot, said moveable handle and said actuation member separated by a pivot point, whereby movement of said movable handle actuates said actuation member and places the bone clamp in on of a clamped and an unclamped position;

a second clamp member, wherein said second clamp member comprises; a stationary handle and a guide member said stationary handle and said guide member separated by said pivot point, wherein said first clamp member is pivotally attached to said second clamp member at said pivot point, said guide member including a support arm with a first gripping point affixed thereto;

a clamp plunger operably connected to the actuation member clamp plunger, said clamp plunger slidably connected to said guide member and having a first and second fixed flange affixed thereto; and a ratchet mechanism for controlling actuation of said first clamp member, said ratchet mechanism comprising a plurality of ratchet teeth having a plurality of ratchet peaks and curved ratchet valleys between said peaks; and wherein, said slot on said Y-shaped end is sized to accommodate said clamp plunger such that said Y-shaped end is in contact with one of said first flange and second flange such that the said clamp plunger is movable between clamped and unclamped positions.

* * * * *